(12) United States Patent
Liu (10) Patent No.: US 12,195,835 B2
(45) Date of Patent: Jan. 14, 2025

(54) METHOD FOR PREPARING MAGNESIUM ALLOY BONE SCREW BAR VIA ROOM-TEMPERATURE ROTARY FORGING UNDER ALTERNATING MAGNETIC FIELD IN CONJUNCTION WITH CRYOGENIC PROCESSING AND MAGNESIUM ALLOY BONE SCREW PRODUCT

(71) Applicant: Hua Rong Ke Chuang Biotechnology(Tian Jin) Co., Ltd., Tianjin (CN)

(72) Inventor: Lina Liu, Tianjin (CN)

(73) Assignee: Hua Rong Ke Chuang Biotechnology (Tian Jin) Co., Ltd, Tianjin (CN)

( * ) Notice: Subject to any disclaimer, the term of this patent is extended or adjusted under 35 U.S.C. 154(b) by 0 days.

(21) Appl. No.: 18/234,545

(22) Filed: Aug. 16, 2023

(65) Prior Publication Data

US 2024/0060166 A1    Feb. 22, 2024

(30) Foreign Application Priority Data

Aug. 17, 2022    (CN) .......................... 202210984614.2

(51) Int. Cl.
*C22F 1/06*      (2006.01)
*A61B 17/86*     (2006.01)
(Continued)

(52) U.S. Cl.
CPC .............. *C22F 1/06* (2013.01); *A61B 17/866* (2013.01); *A61L 31/022* (2013.01); *B21J 1/06* (2013.01); *C22C 23/04* (2013.01)

(58) Field of Classification Search
None
See application file for complete search history.

(56) References Cited

U.S. PATENT DOCUMENTS

2004/0073401 A1    4/2004   Batzinger et al.
2014/0225042 A1    8/2014   In et al.

FOREIGN PATENT DOCUMENTS

CN     101745592 A    6/2010
CN     104576276 A    4/2015
(Continued)

OTHER PUBLICATIONS

English language machine translation of CN-114574791-B. Generated Jul. 27, 2024. (Year: 2024).*

(Continued)

*Primary Examiner* — Brian D Walck
(74) *Attorney, Agent, or Firm* — Wood, Phillips, Katz, Clark & Mortimer (57) ABSTRACT

The present application relates to the technical field of material processing, and especially relates to a method for preparing a magnesium alloy bone screw bar via room-temperature rotary forging under alternating magnetic field in conjunction with cryogenic processing and a magnesium alloy bone screw product. The method specifically comprises the following steps: preparing an ingot, extruding the ingot into a magnesium-zinc-manganese alloy bar, performing room-temperature rotary forging under alternating magnetic field for plastic deformation, wherein the strength and hardness of the magnesium-zinc-manganese alloy are improved by the work hardening effect of magnesium alloy at room temperature, and meanwhile the microstructure is regulated; additionally, via the former and later cryogenic processing, the grain size and grain orientation uniformity can be effectively regulated in the magnesium alloy microstructure, and the magnesium alloy is effectively improved in plastic deformation ability, strength and corrosion resistance, and finally a magnesium alloy bone screw bar is obtained with excellent comprehensive properties in mechanical properties, corrosion resistance and biocompat- (Continued)

ibility, which can be mechanically processed into a magnesium alloy bone screw product.

2 Claims, 6 Drawing Sheets

(51) Int. Cl.
*A61L 31/02* (2006.01)
*B21J 1/06* (2006.01)
*C22C 23/04* (2006.01)

(56) References Cited

FOREIGN PATENT DOCUMENTS

| CN | 104646579 A | | 5/2015 |
|----|-------------|---|--------|
| CN | 105331911 A | | 2/2016 |
| CN | 108774720 A | | 11/2018 |
| CN | 114318187 A | | 4/2022 |
| CN | 114574791 B | * | 12/2022 |
| JP | 2013034348 A | | 2/2013 |

OTHER PUBLICATIONS

Prakash et al. "Influence of cryogenic treatment on the performance of micro-EDM tool electrode in machining of magnesium alloy AZ31B." Materials Today: Proceedings 39 (2021) 1198-1201. Available online Apr. 18, 2020. (Year: 2020).*

* cited by examiner

METHOD FOR PREPARING MAGNESIUM ALLOY BONE SCREW BAR VIA ROOM-TEMPERATURE ROTARY FORGING UNDER ALTERNATING MAGNETIC FIELD IN CONJUNCTION WITH CRYOGENIC PROCESSING AND MAGNESIUM ALLOY BONE SCREW PRODUCT

CROSS-REFERENCE TO RELATED APPLICATION(S)

This application claims priority to Chinese Patent Application No. 202210984614.2 filed Aug. 17, 2022, the disclosure of which is incorporated herein by reference in its entirety.

TECHNICAL FIELD

The present application belongs to the technical field of new materials and material processing, and especially relates to a method for preparing a magnesium alloy bone screw bar via room-temperature rotary forging under alternating magnetic field in conjunction with cryogenic processing, and a magnesium alloy bone screw product.

BACKGROUND

Metal magnesium and its alloy can be degraded in animal body fluid, and the corroded and degraded products can be absorbed or excreted from the body by the animal's metabolically circulatory system, and thus nothing remains in the body to cause harm. Due to the degradability in animals, the magnesium alloy can be used as medical implant materials. The typical magnesium alloy medical implant materials include magnesium alloy cardiovascular stent materials, magnesium alloy bone plate materials, magnesium alloy guided bone regeneration membranes, magnesium alloy internal fixations, etc. For example, patent CN112618120A provides a completely degradable magnesium alloy cardiovascular stent and specific solutions for the structure and function of the stent. Patent CN114262831A provides a method for preparing a magnesium alloy bone plate and 3D printing powders therefor, mainly describing the method for preparing a magnesium alloy bone plate via laser 3D printing. Patent CN113384755A provides a bioactive degradable magnesium alloy guided bone regeneration membrane and a processing method for its dense pores. Patent CN112281037A provides a degradable magnesium alloy femoral internal fixation screw and a preparation method thereof, wherein by using pure magnesium ingots, zinc granules, magnesium-calcium master alloy and magnesium-manganese master alloy as raw materials, and via the methods of smelting, solid solution treatment and hot extrusion, the Mg—Zn—Ca—Mn alloy is obtained with excellent mechanical properties and low degradation rate, and a femoral internal fixation screw is designed and processed based on this magnesium alloy material. In addition, there are many literatures and patents for studying and developing technologies about controlling the degradation behavior of degradable magnesium alloy by surface treatment, improving the corrosion properties and biocompatibility of alloys by adding rare earth elements, and processing magnesium alloy materials into various shapes by pressure. These technologies contribute lots of basic work for the preparation, development and application of degradable magnesium alloys.

The requirements for comprehensive properties of magnesium alloy are very strict when used as implant materials in animals, and the physical, chemical, mechanical, and biological properties should all satisfy the application requirements of serving animals inside the body. Besides, because of the degradation characteristics, degradation products of the magnesium alloy are also strictly required, which cannot have adverse effects on animal cells, tissues, and organs. Hence, magnesium alloys of different types, states, and properties are suitable for different implantation sites; for example, there are magnesium alloy intended for cardiovascular stents, magnesium alloy intended for bone tissue engineering, magnesium alloy intended for bone screws, and magnesium alloy intended for anastomats. These different applications require different materials, different processing methods and different properties to realize the use in specific body parts. The diversity of organisms determines the diversity and particularity of magnesium alloy implant materials. It is necessary to study and develop special magnesium alloy materials and implant devices for such particularity.

Some special preparation methods have been developed and applied for magnesium alloy implant materials aiming at different body parts. For example, patent CN112281037A uses preparation methods of smelting, solid solution treatment and hot extrusion to prepare a magnesium alloy femoral internal fixation screw. Patent CN113621858A uses powder atomization and selective laser melting to obtain a degradable magnesium alloy bone screw which is antibacterial and inhibits tumor proliferation. Patent CN111451944A uses shot peening to process degradable magnesium alloy bone screws, so as to obtain magnesium alloy bone screws with different hardness. Patent CN210811451U carries out development on the structure, shape and patterns of degradable magnesium alloy bone screws, and obtains magnesium alloy bone screws with different structures. In addition, some patents carry out research and development on the surface treatment of magnesium alloy bone screws. These studies provide the processes required by different bone screw products from various aspects including material composition, preparation technology, and processing methods, satisfying the use needs of magnesium alloy bone screw in different aspects.

In the practical applications, the magnesium alloy bone screw should meet use requirements in several performance characteristics before subjected to further clinical trials. These characteristic requirements include that: the magnesium alloy bone screw must achieve sufficient strength (the bone screw with high yield strength does not deform when used), sufficient hardness (the bone screw thread does not develop wear after screwed in or out of the animal bone for many times), good plasticity (the bone screw has high elongation and is not easy to break), excellent corrosion resistance (the bone screw has controllable degradation rate in body fluid), and good biocompatibility (the bone screw has weak cytotoxicity and achieve non-toxic). The matching of mechanical properties, corrosion properties and biological properties of the bone screw demands strictly on the material preparation and processing method of magnesium alloy bone screw, and the conventional material preparation technologies and methods cannot satisfy the use requirements of magnesium alloy bone screw implant, and it is necessary to use a new preparation and processing method.

Generally, magnesium alloy bars are used as raw materials for the processing of magnesium alloy bone screw. The magnesium alloy has difficulty in plastic deformation due to its hexagonal close-packed crystal structure. Accordingly, the plastic deformation of magnesium alloy bars is usually realized via hot extrusion process. Such deformation method can effectively guarantee the forming of magnesium alloy bars, but hard to guarantee the work hardening effect of magnesium alloy because hot-extruded magnesium alloys are prone to dynamic recrystallization softening behavior, and thus heat strengthening process is usually needed to improve the strength. However, the heat strengthening technology and process only has an effect on magnesium alloys with specific compositions, and lots of magnesium alloys cannot obtain significant heat strengthening effect, especially the biomedical magnesium alloy. Due to the specificity of added alloy elements and material characteristics, the biomedical magnesium alloy is difficult to improve strength through heat processing. Therefore, the biomedical magnesium alloy bars, especially the magnesium alloy used as bone screws, require excellent comprehensive mechanical properties; it is an important technical problem for the magnesium alloy bone screw bars about how to obtain good plastic deformation ability, guarantee strength and hardness of magnesium alloy bone screws, improve corrosion resistance and obtain biocompatibility, harmonically.

SUMMARY

In view of the technical problems, in the present application, the magnesium alloy bar is rotary-forged at room temperature for plastic deformation, and applied with alternating magnetic field during the rotary forging; under the synergistic effect of alternating magnetic field and room-temperature rotary forging, the grain size and grain orientation uniformity can be regulated in the magnesium alloy microstructure, and the work hardening effect can be stabilized, and via the cryogenic processing before and after the rotary forging, the magnesium alloy bar is effectively improved in plastic deformation ability, strength and corrosion resistance, and finally a magnesium alloy bone screw bar and a bone screw product are obtained with excellent comprehensive properties in mechanical properties, corrosion resistance and biocompatibility.

The present application provides a method for preparing a magnesium alloy bone screw bar via room-temperature rotary forging under alternating magnetic field in conjunction with cryogenic processing, comprising the following steps:
  S1: preparing an ingot: casting magnesium-zinc-manganese alloy into an ingot, wherein the ingot has a composition satisfying that: 0.5%-1.5% of Zn, 0.2%-1.2% of Mn, Si≤0.01, Al≤0.01, Fe≤0.01, Cu≤0.002, Ni≤0.001, and a remainder of Mg; a grain size is controlled at less than or equal to 200 μm;
  S2: preparing a magnesium-zinc-manganese alloy bar: holding the ingot at 380-420° C. for 3-24 h, and then extruding the ingot with an extrusion ratio controlled at 16-40 to obtain a magnesium-zinc-manganese alloy bar with a grain size of less than or equal to 50 μm;
  S3: performing cryogenic processing: subjecting the magnesium-zinc-manganese alloy bar to cryogenic processing for 1-12 h at a liquid nitrogen temperature controlled at −195° C. to −215° C., and returning to room temperature after the cryogenic processing to obtain a cryogenic processing magnesium-zinc-manganese alloy bar;
  S4: performing room-temperature rotary forging under alternating magnetic field: applying alternating magnetic field of 1000-10000 Hz around the cryogenic processing magnesium-zinc-manganese alloy bar, and simultaneously subjecting the cryogenic processing magnesium-zinc-manganese alloy bar to room-temperature rotary forging in a rotary forging machine with a deformation controlled at 5%-50% to obtain a room-temperature rotary forging magnesium-zinc-manganese alloy bar;
  S5: repeating steps S3-S4 until the magnesium-zinc-manganese alloy bar is rotary-forged to a required diameter; and
  S6: performing subsequent heat processing: placing the magnesium-zinc-manganese alloy bar obtained in step S5 in an electric furnace at 275-375° C. and holding for 1-2 h, and then cooling to room temperature to obtain the magnesium alloy bone screw bar. The temperature holding in step S6 is performed to obtain a bar with coordinated and appropriate hardness, strength and plasticity.

Furthermore, in step S5, when obtaining the required diameter via the room-temperature rotary forging, the last room-temperature rotary forging has a deformation of at least 20%, guaranteeing sufficient room-temperature deformation and work hardening effect.

Furthermore, in step S6, the holding time for the subsequent heat processing is replaced with 2-12 h, the purpose of which is to obtain a bar with outstanding elongation.

The present application also provides a magnesium alloy bone screw product, which is obtained by mechanically processing the magnesium alloy bone screw bar according to specific requirements on the shape, length and diameter of a bone screw.

Furthermore, the magnesium alloy bone screw bar is subjected to cryogenic processing again before the mechanical processing, wherein the magnesium alloy bone screw bar is cooled to −196° C. to −215° C. and held for 1-12 h. The stability between dislocations and dislocations or dislocations and other microstructures, generated during the rotary forging of magnesium alloy, can be guaranteed, thereby ensuring the stability of the work hardening effect of the bone screw bar, giving the magnesium alloy bone screw bar excellent comprehensive mechanical properties.

The beneficial effects of the present application are described below.

(1) Compared with room-temperature rotary forging in conjunction with cryogenic processing, the method of room-temperature rotary forging under alternating magnetic field in conjunction with cryogenic processing has the beneficial effects as follows: the alternating magnetic field will bring different electromagnetic induction effects to different metal materials, and with respect to magnesium alloy, a synergistic effect can be brought by the simultaneous action of alternating magnetic field and rotary forging, the mechanism of which lies in the positive influence on internal microstructure:
  ① it is beneficial for dislocations to generate cross-slip on different slip planes, thereby facilitating the generation of plastic deformation;
  ② magnesium alloy is prone to partial dislocations and stacking faults, the partial dislocations will undergo dislocation reactions to form perfect dislocations which can easily move on different slip planes, and the alternating magnetic field can accelerate the dislocation reactions between partial dislocations; and
  ③ due to the dislocation reactions and dislocation movement, the dislocation pileup is reduced which is caused by grain boundaries influencing the near dislocations; the dislocation pileup will lead to stress concentration, resulting in microcracks in the material and accordingly cracks in the magnesium alloy during plastic deformation; the alternating magnetic field can effectively change the dislocation configuration in microstructure by influencing and regulating the dislocations; the single rotary forging deformation can effectively improve the strength and hardness of magnesium alloy, resulting in work hardening effect, but does not facilitate the continuation and stability of plastic deformation, or even reduces the plastic deformation of magnesium alloy bars to a certain extent; by regulating the dislocation configuration inside magnesium alloy via the alternating magnetic field, the plastic deformation ability is improved for the magnesium alloy during the room-temperature rotary forging, and the comprehensive mechanical properties of the magnesium alloy are synergistically improved such as strength and plasticity.

However, Chinese patent CN104646579B discloses a high-frequency rotary precision forging composite method for manufacturing metal composite tubes/bars, wherein it is mentioned that a high-frequency rotary precision forging machine 6 applies alternating magnetic field to a magnetic hammer head, and the frequency of rotary forging is increased based on the repulsion and attraction of magnetic field. In this patent, magnetic field is applied to the hammer head of rotary forging machine rather than the machined workpiece, and by utilizing magnetic field during the operation, the rotary forging machine operating becomes a high-frequency rotary precision forging machine, distinguished from the ordinary rotary forging machine. In the present application, the magnesium alloy bar (i.e., the machined workpiece) is applied with alternating magnetic field along with common rotary forging, and therefore, under the synergistic effect of the alternating magnetic field and rotary forging on magnesium alloy, the microstructure of magnesium alloy can be regulated, and furthermore, the comprehensive mechanical properties of the magnesium alloy are synergistically improved such as strength and plasticity.

(2) Compared with room-temperature rotary forging in conjunction with conventional annealing, the method of room-temperature rotary forging under alternating magnetic field in conjunction with cryogenic processing has the beneficial effects as follows: in a case of room-temperature rotary forging in conjunction with conventional annealing, the amount of dislocations will decrease rapidly, impairing the strengthening effect, and more importantly, the grains that have been crushed and refined by rotary forging will recrystallize and grow during the high-temperature annealing, losing the strengthening effect for fine grains; thereby, the work hardening effect after room-temperature rotary forging will disappear rapidly during the subsequent heating annealing, and the plasticity is improved at the sacrifice of mechanical properties such as strength and hardness; the cryogenic processing can effectively stabilize the configuration and amount of dislocations in the microstructure of magnesium alloy after the synergetic action of alternating magnetic field and room-temperature rotary forging, and more stably maintain the strengthening effect between dislocations and grain boundaries or alloy phases, and meanwhile maintain the grain breaking and refining effect; the cryogenic processing can effectively stabilize and maintain the work hardening effect, and realize the simultaneous improvement of strength and plasticity, which are contradictory mechanical properties of magnesium alloys.

(3) After room-temperature rotary forging under alternating magnetic field in conjunction with cryogenic processing, the dislocations and stacking faults in microstructure of magnesium alloy can interact with grain boundaries, other dislocations, and second phases, improving the strengthening effect on the magnesium alloy, and under the cryogenic action, such strengthening effect can be further maintained stably, and such strengthening effect can be manifested as improving the wear resistance and bite force of the magnesium alloy bone screw product when rotating in the animal bone; additionally, due to the fine grain size and uniform grain orientation in microstructure, the magnesium alloy is improved in corrosion and degradation resistance, showing improved degradation behavior in animal body fluid macroscopically.

(4) As known to all, applying magnetic field to molten metal or chemical solution, namely, the liquid substance, is easy to obtain obvious beneficial effects, such as improving the uniformity of the melt composition, improving the alloying effect of the melt, improving the toughness of ingots from the melt casting, and improving the conductivity of alloy, etc. However, there are few studies on applying magnetic field to solid metal materials; in the present application, based on the microstructure evolution characteristics of solid magnesium alloy bar, the force field of rotary forging is coupled with alternating magnetic field, and unexpected technical effects are brought to the solid magnesium alloy bar via the combined effects of magnetic field and force field, that is, the cooperation of those two fields bring obvious effects on the solid phase transformation and microstructure evolution of the magnesium alloy, and bring an effect of 1 (magnetic field)+1 (force field)>2 rather than simple superposition.

(5) In the present application, the cryogenic processing is performed before every rotary forging, and the maximum deformation of magnesium alloy is thus significantly improved, reaching as high as 50%, which is the advantage of cryogenic processing, and other methods and processes are difficult to achieve such a high deformation for magnesium alloy.

(6) The alternating magnetic field, room-temperature rotary forging, cryogenic processing and subsequent heat processing technologies can be realized in related special equipment in the production process of magnesium-zinc-manganese alloy. The production process is short, and the process stability is good, which is suitable for industrialization. Under the synergistic effect of alternating magnetic field and room-temperature rotary forging, the grain size and grain orientation uniformity can be regulated in the magnesium alloy microstructure, and the work hardening effect can be stabilized, and via the cryogenic processing before and after the rotary forging, the magnesium alloy bar is effectively improved in plastic deformation ability, strength and corrosion resistance, and finally a magnesium alloy bone screw bar is obtained with excellent comprehensive properties in mechanical properties, corrosion resistance and biocompatibility.

DETAILED DESCRIPTION

For clearer technical methods, advantages and objects of the present application, the technical solutions of the present application will be described in detail below. However, the described content is only preferred embodiments of the present application. Without departing from the spirit and concept of the present application, any modification or replacement of the steps or conditions of the present application shall fall within the protection scope of the present application.

Comparative Examples 1 and 2

Figure 1:
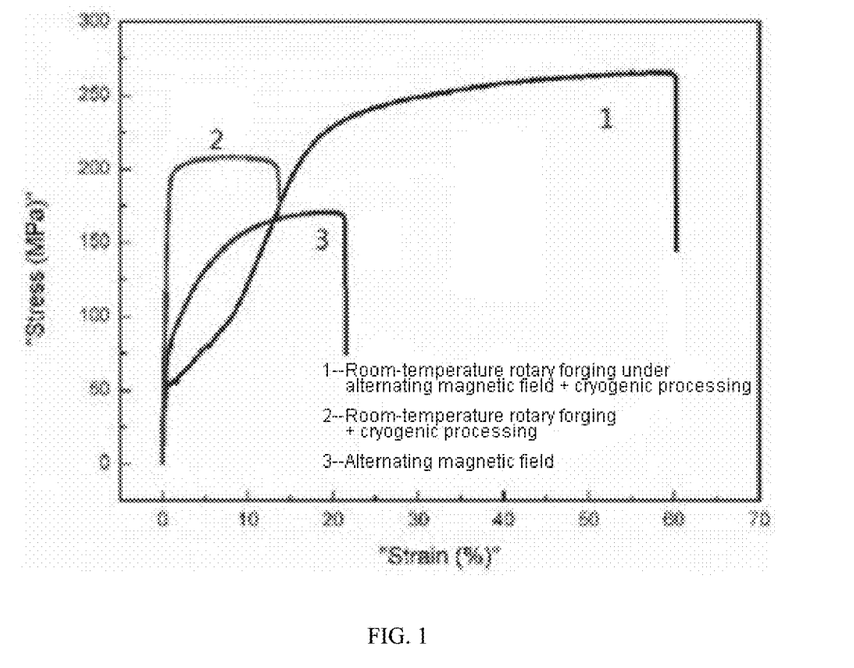
FIG. 1 shows a comparison result of magnesium-zinc-manganese alloys after different processing techniques in strength and elongation.
Figure 9:
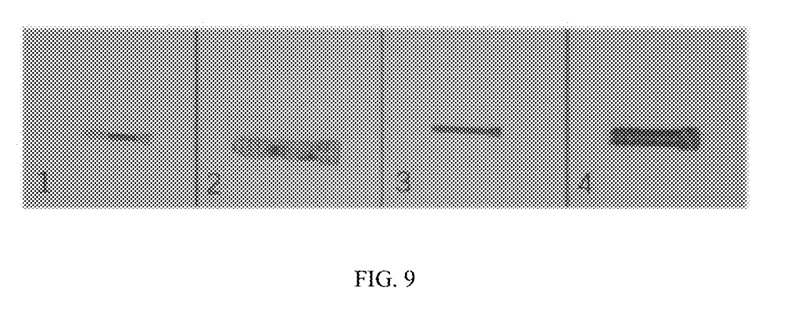
FIG. 9 shows degradation comparison between magnesium alloy bone screw products obtained by the action of single alternating magnetic field and the preparation method of the present application.

Comparative Example 1 provides a magnesium-zinc-manganese alloy bar formed by hot extrusion, and only under the action of single alternating magnetic field, the magnesium-zinc-manganese alloy bar has a tensile mechanical property as shown by curve 3 in FIG. 1. Comparative Example 2 provides a magnesium-zinc-manganese alloy bar formed by hot extrusion, and after room-temperature rotary forging in conjunction with cryogenic processing, the magnesium-zinc-manganese alloy bar has a tensile mechanical property as shown by curve 2 in FIG. 1. The magnesium alloy bar obtained in Comparative Example 1 was mechanically processed into a bone screw product, and the bone screw product was degraded in simulated body fluid for 15 days, the corrosion degree of which is shown in FIG. 9(1)(2).

Example 1

A method for preparing a magnesium alloy bone screw bar via room-temperature rotary forging under alternating magnetic field in conjunction with cryogenic processing includes the following steps:

- S1: preparing an ingot: magnesium-zinc-manganese alloy was cast into an ingot, wherein the ingot had a composition satisfying that: 1.5% of Zn, 1.2% of Mn, Si≤0.01, Al≤0.01, Fe≤0.01, Cu≤0.002, Ni≤0.001, and a remainder of Mg; a grain size was controlled at less than or equal to 100 μm;
- S2: preparing a magnesium-zinc-manganese alloy bar: the ingot was held at 420° C. for 24 h, and then extruded with an extrusion ratio controlled at 40 to obtain a magnesium-zinc-manganese alloy bar with a grain size of 20-30 μm;
- S3: performing cryogenic processing: the magnesium-zinc-manganese alloy bar was subjected to cryogenic processing for 12 h at a liquid nitrogen temperature controlled at −215° C., and returned to room temperature after the cryogenic processing to obtain a cryogenic processing magnesium-zinc-manganese alloy bar;
- S4: performing room-temperature rotary forging under alternating magnetic field: the cryogenic processing magnesium-zinc-manganese alloy bar was applied with alternating magnetic field of 10000 Hz by an alternating magnetic field generator of Bamac Electric, and simultaneously subjected to room-temperature rotary forging in a rotary forging machine with a deformation controlled at 50%; the force of rotary forging was applied along with the action of alternating magnetic field to obtain a room-temperature rotary forging magnesium-zinc-manganese alloy bar;
- S5: steps S3-S4 were repeated until the magnesium-zinc-manganese alloy bar was rotary-forged to a required diameter; and
- S6: performing subsequent heat processing: the magnesium-zinc-manganese alloy bar obtained in step S5 was placed in an electric furnace at 375° C. and held for 2 h, and then cooled to room temperature to obtain the magnesium alloy bone screw bar.

Figure 2:
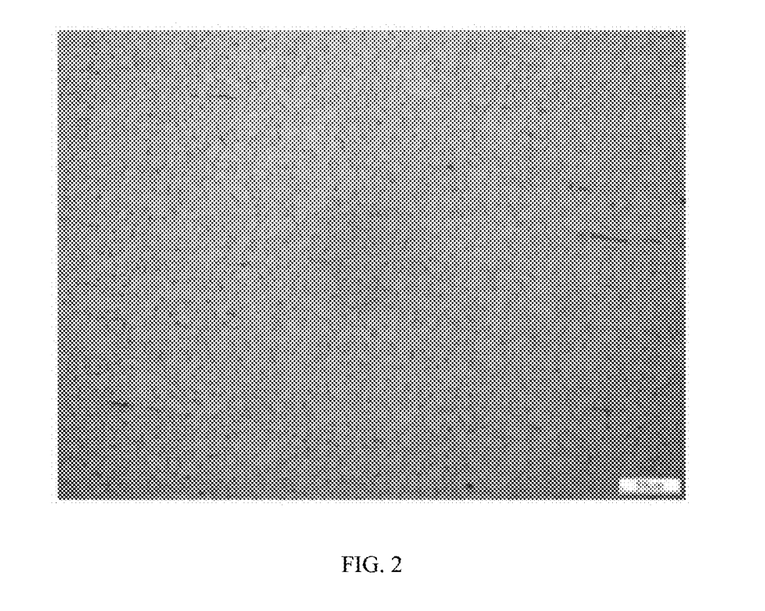
FIG. 2 is a microstructural picture showing a magnesium-zinc-manganese alloy bar under the action of single alternating magnetic field.
Figure 3:
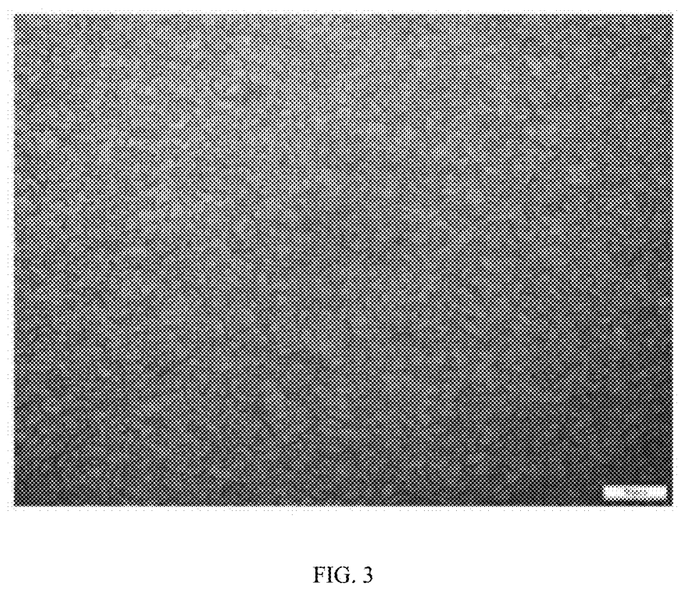
FIG. 3 is a microstructural picture showing a magnesium-zinc-manganese alloy bar after room-temperature rotary forging in conjunction with cryogenic processing.
Figure 4:
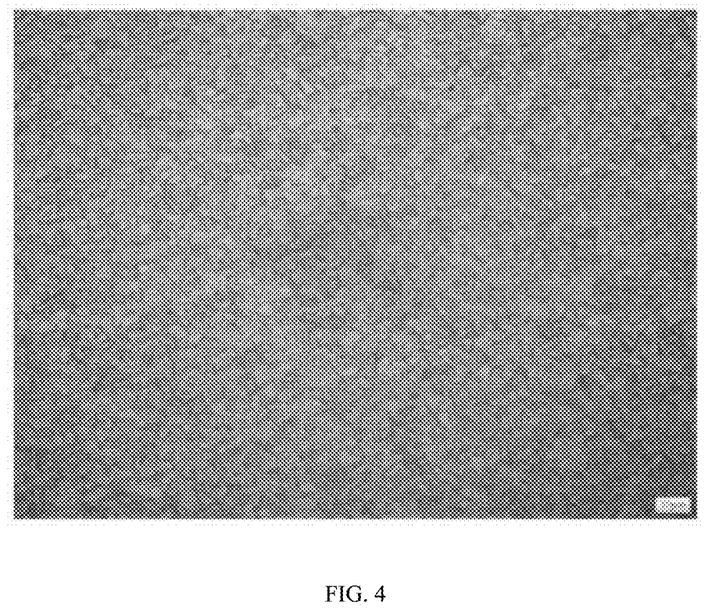
FIG. 4 is a microstructural picture showing a magnesium-zinc-manganese alloy bar after room-temperature rotary forging under alternating magnetic field in conjunction with cryogenic processing.
Figure 5:
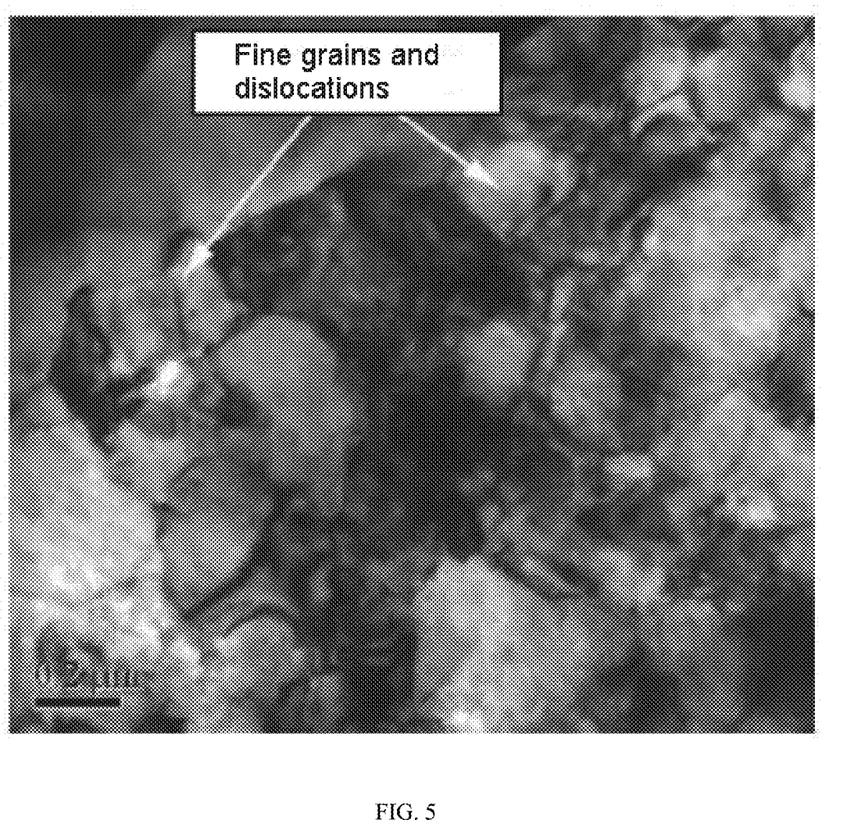
FIG. 5 is a morphological picture showing fine grains and dislocation tangles after room-temperature rotary forging under alternating magnetic field in conjunction with cryogenic processing.
Figure 6:
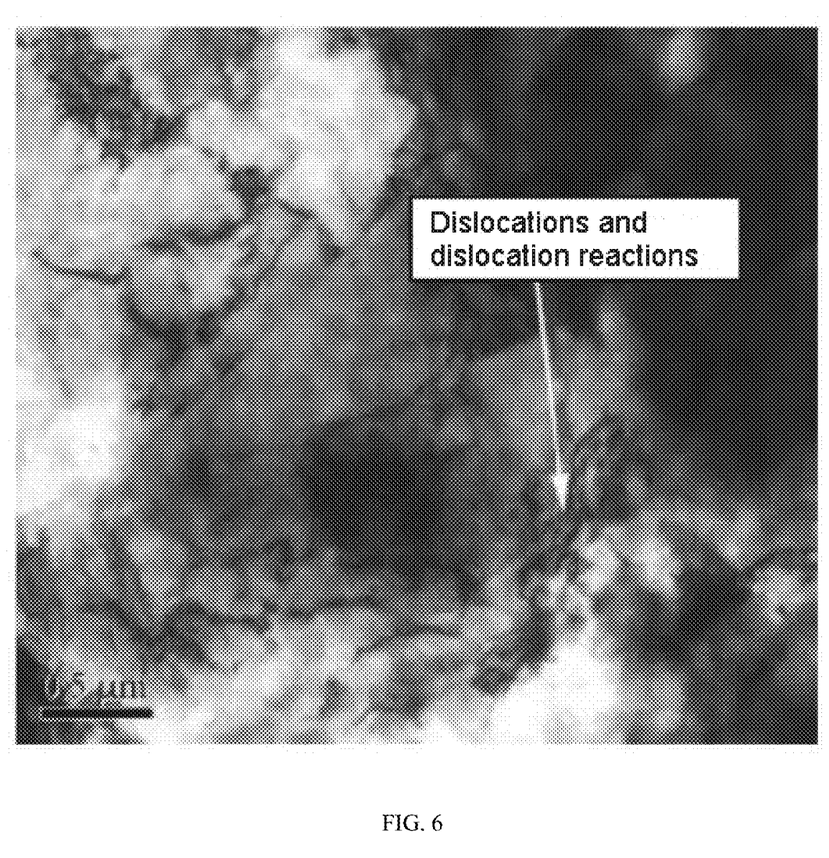
FIG. 6 is a morphological picture showing dislocations and dislocation reactions after room-temperature rotary forging under alternating magnetic field in conjunction with cryogenic processing.
Figure 7:
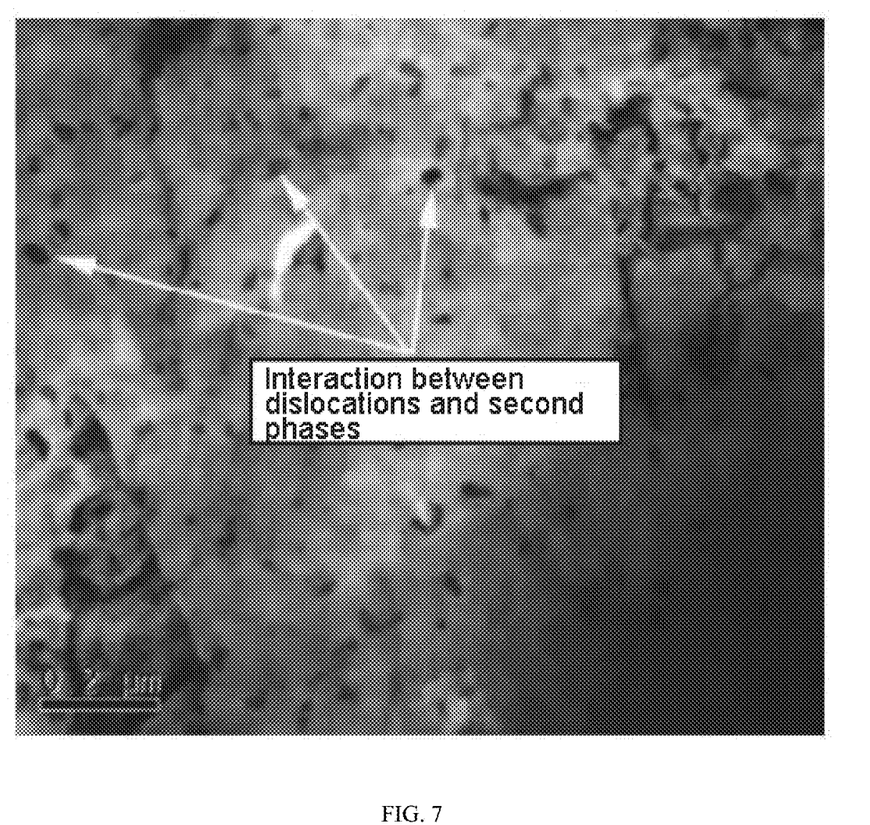
FIG. 7 is a morphological picture showing interaction between dislocations and fine alloy phases after room-temperature rotary forging under alternating magnetic field in conjunction with cryogenic processing.

In the method, the last room-temperature rotary forging had a deformation of 26.5%, guaranteeing sufficient room-temperature deformation to achieve work hardening effect; the microstructure is shown in FIG. 3-FIG. 7. FIG. 2 shows the microstructure of magnesium alloy under the action of single alternating magnetic field, and it can be observed that the magnesium alloy has an equiaxial recrystallization structure and the grain size is not uniform; the single alternating magnetic field can be beneficial to the plastic deformation of magnesium alloy, but have limited effect to improve its strength. After room-temperature rotary forging under alternating magnetic field, the grains are obviously broken, the grains are further refined, and especially the subgrains are refined, thus obtaining the effect that the strength is improved by grain refinement (FIG. 3); then after cryogenic processing, the morphology of such fine grains can be effectively guaranteed (FIG. 4), which thus facilitates the subsequent plastic deformation and strength improvement. After room-temperature rotary forging under alternating magnetic field in conjunction with cryogenic processing, the dislocations of magnesium alloy generated by plastic deformation can interact with grain boundaries, other dislocations, and second phases (FIG. 5-FIG. 7), improving the strengthening effect on the magnesium alloy, and under the cryogenic action, such strengthening effect can be further maintained stably, and such strengthening effect can be manifested as improving the wear resistance and bite force of the magnesium alloy bone screw product when rotating in the animal bone.

A tensile curve of the magnesium alloy bone screw bar obtained in this example is shown by curve 1 in FIG. 1. From the comparison of curve 1, curve 2 and curve 3 in FIG. 1, it can be seen that the plastic deformation capacity of magnesium alloy is greatly improved by the method of room-temperature rotary forging under alternating magnetic field in conjunction with cryogenic processing. As shown by curve 3, the plastic elongation of magnesium alloy reaches 22% under the action of single alternating magnetic field; with respect to curve 2, after room-temperature rotary forging in conjunction with cryogenic processing, the elongation of magnesium alloy is about 14%, but the strength is increased to 208.4 MPa from 171.2 MPa; with respect to curve 1, via performing room-temperature rotary forging along with alternating magnetic field and combining with cryogenic processing, the elongation of magnesium alloy can reach nearly 60%, thus achieving large plastic deformation, and meanwhile, the strength can reach 268.7 MPa. Therefore, the performance shown by curve 1, whether strength or plasticity, is not a simple superposition of the strength or plasticity of curve 2 and curve 3, but a qualitative leap, that is, a synergistic effect. Specifically, the strength can be improved by 57% and 29% via the method of room-temperature rotary forging under alternating magnetic field in conjunction with cryogenic processing (curve 1) compared with the single alternating magnetic field (curve 3) and the room-temperature rotary forging in conjunction with cryogenic processing (curve 2), respectively; the elongation is increased by 2.7 times and 4.2 times respectively. In general, the strength and plasticity of the material are significantly improved simultaneously by the room-temperature rotary forging under alternating magnetic field in conjunction with cryogenic processing, and the synergistic effect is remarkable.

Figure 8:
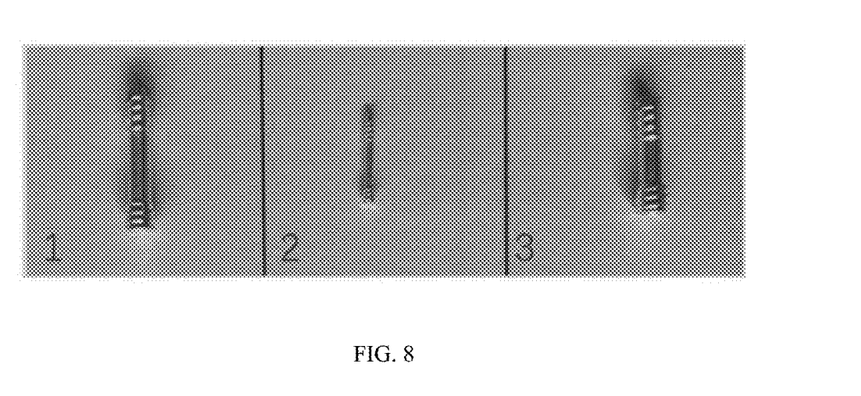
FIG. 8 shows magnesium alloy bone screw products obtained by mechanically processing magnesium alloy bone screw bars obtained in Examples 1-3 of the present application.

The magnesium alloy bone screw bar obtained from the above preparation method was mechanically processed into a magnesium alloy bone screw product, which had a screw shape with thread, and a length of 20 mm and a diameter of 4 mm, as shown in FIG. 8(1).

As shown in FIG. 9, FIG. 9(1)(2) show the corrosion situation of the bone screw products after soaked in simulated body fluid for 15 days, which are obtained from the magnesium alloy bar after alternating magnetic field in Comparative Example 1; FIG. 9(3)(4) show the corrosion situation of the bone screw products after soaked in simulated body fluid for 15 days, which are obtained from the magnesium alloy bar after room-temperature rotary forging under alternating magnetic field in conjunction with cryogenic processing in this example; the bone screw products shown in FIG. 9(1) and FIG. 9(3) both have a diameter of 1 mm and a length of 14 mm, and the bone screw products shown in FIG. 9(2) and FIG. 9(4) both have a diameter of 4 mm and a length of 20 mm. It can be seen from the comparison that after soaked in simulated body fluid for 15 days, the magnesium alloy bone screw products obtained only via alternating magnetic field are obviously corroded, while the magnesium alloy bone screw products obtained via room-temperature rotary forging under alternating magnetic field in conjunction with the cryogenic processing are not corroded.

Example 2

A method for preparing a magnesium alloy bone screw bar via room-temperature rotary forging under alternating magnetic field in conjunction with cryogenic processing includes the following steps:
S1: preparing an ingot: magnesium-zinc-manganese alloy was cast into an ingot, wherein the ingot had a composition satisfying that: 0.5% of Zn, 0.2% of Mn, Si≤0.01, Al≤0.01, Fe≤0.01, Cu≤0.002, Ni≤0.001, and a remainder of Mg; a grain size was controlled at less than or equal to 200 μm;
S2: preparing a magnesium-zinc-manganese alloy bar: the ingot was held at 380° C. for 3 h, and then extruded with an extrusion ratio controlled at 16 to obtain a magnesium-zinc-manganese alloy bar with a grain size of less than or equal to 50 μm;
S3: performing cryogenic processing: the magnesium-zinc-manganese alloy bar was subjected to cryogenic processing for 1 h at a liquid nitrogen temperature controlled at −195° C., and returned to room temperature after the cryogenic processing to obtain a cryogenic processing magnesium-zinc-manganese alloy bar;
S4: performing room-temperature rotary forging under alternating magnetic field: the cryogenic processing magnesium-zinc-manganese alloy bar was applied with alternating magnetic field of 1000 Hz by an alternating magnetic field generator of Bamac Electric, and simultaneously subjected to room-temperature rotary forging in a rotary forging machine with a deformation controlled at 5%; the force of rotary forging was applied along with the action of alternating magnetic field to obtain a room-temperature rotary forging magnesium-zinc-manganese alloy bar;
S5: steps S3-S4 were repeated until the magnesium-zinc-manganese alloy bar was rotary-forged to a required diameter; and
S6: performing subsequent heat processing: the magnesium-zinc-manganese alloy bar obtained in step S5 was placed in an electric furnace at 275° C. and held for 1 h, and then cooled to room temperature to obtain the magnesium alloy bone screw bar.

In the method, the last room-temperature rotary forging had a deformation of 20.6%, guaranteeing sufficient room-temperature deformation to achieve work hardening effect.

The magnesium alloy bone screw bar obtained from the above preparation method was mechanically processed into a magnesium alloy bone screw product, which had a screw shape with thread, and a length of 14 mm and a diameter of 1 mm, as shown in FIG. 8(2).

Example 3

A method for preparing a magnesium alloy bone screw bar via room-temperature rotary forging under alternating magnetic field in conjunction with cryogenic processing includes the following steps:
S1: preparing an ingot: magnesium-zinc-manganese alloy was cast into an ingot, wherein the ingot had a composition satisfying that: 1.0% of Zn, 0.6% of Mn, Si≤0.01, Al≤0.01, Fe≤0.01, Cu≤0.002, Ni≤0.001, and a remainder of Mg; a grain size was controlled at less than or equal to 100 μm;
S2: preparing a magnesium-zinc-manganese alloy bar: the ingot was held at 400° C. for 12 h, and then extruded with an extrusion ratio controlled at 16 to obtain a magnesium-zinc-manganese alloy bar with a grain size of less than or equal to 50 pin;
S3: performing cryogenic processing: the magnesium-zinc-manganese alloy bar was subjected to cryogenic processing for 6 h at a liquid nitrogen temperature controlled at −196° C., and returned to room temperature after the cryogenic processing to obtain a cryogenic processing magnesium-zinc-manganese alloy bar;
S4: performing room-temperature rotary forging under alternating magnetic field: the cryogenic processing magnesium-zinc-manganese alloy bar was applied with alternating magnetic field of 5000 Hz by an alternating magnetic field generator of Bamac Electric, and simultaneously subjected to room-temperature rotary forging in a rotary forging machine with a deformation controlled at 35%; the force of rotary forging was applied along with the action of alternating magnetic field to obtain a room-temperature rotary forging magnesium-zinc-manganese alloy bar;

S5: steps S3-S4 were repeated until the magnesium-zinc-manganese alloy bar was rotary-forged to a required diameter; and S6: performing subsequent heat processing: the magnesium-zinc-manganese alloy bar obtained in step S5 was placed in an electric furnace at 375° C. and held for 12 h, and then cooled to room temperature to obtain the magnesium alloy bone screw bar.

In the method, the last room-temperature rotary forging had a deformation of 50%, guaranteeing sufficient room-temperature deformation to achieve work hardening effect.

The magnesium alloy bone screw bar obtained from the above preparation method was mechanically processed into a magnesium alloy bone screw product, which had a screw shape with thread, and a length of 18 mm and a diameter of 4 mm, as shown in FIG. 8(3).

Furthermore, the magnesium alloy bone screw bar was subjected to cryogenic processing again before the mechanical processing, wherein it was cooled to −196° C. and held for 6 h.

The examples of the present application have been described in detail. However, the described content is only preferred examples of the present application, and the protection scope of the present application is not limited thereto. On the basis of the present application, any modification or improvement which is obvious for those skilled in the art shall fall within the protection scope of the present application.

What is claimed is:

1. A method for preparing a magnesium alloy bone screw bar via room-temperature rotary forging under alternating magnetic field in conjunction with cryogenic processing, comprising the following steps:
    S1: preparing an ingot: casting magnesium-zinc-manganese alloy into an ingot, wherein the ingot has a composition consisting essentially of 0.5%-1.5% of Zn, 0.2%-1.2% of Mn, and a remainder of Mg; a grain size is controlled at less than or equal to 200 μm;
    S2: preparing a magnesium-zinc-manganese alloy bar: holding the ingot at 380-420° C. for 3-24 hours, and then extruding the ingot with an extrusion ratio controlled at 16-40 to obtain a magnesium-zinc-manganese alloy bar with a grain size of less than or equal to 50 μm;
    S3: performing cryogenic processing: subjecting the magnesium-zinc-manganese alloy bar to cryogenic processing for 1-12 hours at a liquid nitrogen temperature controlled at −195° C. to −215° C., and returning to room temperature after the cryogenic processing to obtain a cryogenic processing magnesium-zinc-manganese alloy bar;
    S4: performing room-temperature rotary forging under alternating magnetic field: applying alternating magnetic field of 1000-10000 Hz around the cryogenic processing magnesium-zinc-manganese alloy bar, and simultaneously subjecting the cryogenic processing magnesium-zinc-manganese alloy bar to room-temperature rotary forging in a rotary forging machine with a deformation controlled at 5%-50% to obtain a room-temperature rotary forging magnesium-zinc-manganese alloy bar;
    S5: repeating steps S3-S4 until the magnesium-zinc-manganese alloy bar is rotary-forged to a required diameter; and
    S6: performing subsequent heat processing: placing the magnesium-zinc-manganese alloy bar obtained in step S5 in an electric furnace at 275-375° C. and holding for 1-2 hours, and then cooling to room temperature to obtain the magnesium alloy bone screw bar;
    wherein in step S5, when obtaining the required diameter via the room-temperature rotary forging, the last room-temperature rotary forging has a deformation of at least 20%.

2. The method for preparing a magnesium alloy bone screw bar via room-temperature rotary forging under alternating magnetic field in conjunction with cryogenic processing, comprising the following steps:
    S1: preparing an ingot: casting magnesium-zinc-manganese alloy into an ingot, wherein the ingot has a composition consisting essentially of 0.5%-1.5% of Zn, 0.2%-1.2% of Mn, and a remainder of Mg; a grain size is controlled at less than or equal to 200 μm;
    S2: preparing a magnesium-zinc-manganese alloy bar: holding the ingot at 380-420° C. for 3-24 hours, and then extruding the ingot with an extrusion ratio controlled at 16-40 to obtain a magnesium-zinc-manganese alloy bar with a grain size of less than or equal to 50 μm;
    S3: performing cryogenic processing: subjecting the magnesium-zinc-manganese alloy bar to cryogenic processing for 1-12 hours at a liquid nitrogen temperature controlled at −195° C. to −215° C., and returning to room temperature after the cryogenic processing to obtain a cryogenic processing magnesium-zinc-manganese alloy bar;
    S4: performing room-temperature rotary forging under alternating magnetic field: applying alternating magnetic field of 1000-10000 Hz around the cryogenic processing magnesium-zinc-manganese alloy bar, and simultaneously subjecting the cryogenic processing magnesium-zinc-manganese alloy bar to room-temperature rotary forging in a rotary forging machine with a deformation controlled at 5%-50% to obtain a room-temperature rotary forging magnesium-zinc-manganese alloy bar;
    S5: repeating steps S3-S4 until the magnesium-zinc-manganese alloy bar is rotary-forged to a required diameter; and
    S6: performing subsequent heat processing: placing the magnesium-zinc-manganese alloy bar obtained in step S5 in an electric furnace at 275-375° C. and holding for 2-12 hours, and then cooling to room temperature to obtain the magnesium alloy bone screw bar;
    wherein in step S5, when obtaining the required diameter via the room-temperature rotary forging, the last room-temperature rotary forging has a deformation of at least 20%.

* * * * *